United States Patent
Schraft et al.

(12)

(10) Patent No.: US 6,902,570 B2
(45) Date of Patent: Jun. 7, 2005

(54) DEVICE AND METHOD FOR CONNECTING HOLLOW ORGANS AND/OR SEALING WALL DEFECTS IN HOLLOW ORGANS

(76) Inventors: Rolf Dieter Schraft, Hildebrandstrasse 11, 70191, Stuttgart (DE); Andrea Hiller, Augustenstrasse 80, 70178, Stuttgart (DE); Jochen Klenk, Bergstrasse 50, 71540, Murrhardt (DE); Joachim Gerd Rein, Kallenbergstrasse 92, 70825, Korntal (DE); Alexander Paul Horke, Behnhofstrasse 68, 74321, Bietigheim-Bissingen (DE)

( * ) Notice: Subject to any disclaimer, the term of this patent is extended or adjusted under 35 U.S.C. 154(b) by 0 days.

(21) Appl. No.: 09/965,159

(22) Filed: Sep. 27, 2001

(65) Prior Publication Data

US 2003/0153931 A1 Aug. 14, 2003

Related U.S. Application Data

(60) Provisional application No. 60/297,127, filed on Jun. 8, 2001.

(51) Int. Cl.[7] .............................................. A61B 17/12
(52) U.S. Cl. ...................................................... 606/144
(58) Field of Search ................................ 606/139, 144, 606/145, 146, 147, 148, 149, 150, 153

(56) References Cited

U.S. PATENT DOCUMENTS

| | | | | |
|---|---|---|---|---|
| 4,357,946 A | | 11/1982 | Dutcher et al. ............. | 128/785 |
| 5,259,395 A | | 11/1993 | Li .............................. | 607/131 |
| 5,356,424 A | | 10/1994 | Buzerak et al. ............. | 606/223 |
| 5,364,408 A | * | 11/1994 | Gordon ....................... | 606/139 |
| 5,470,338 A | * | 11/1995 | Whitfield et al. ........... | 606/144 |
| 5,545,148 A | | 8/1996 | Wurster | |
| 5,665,109 A | * | 9/1997 | Yoon .......................... | 606/144 |
| 5,800,524 A | | 9/1998 | Borghi ........................ | 623/1 |
| 5,820,631 A | * | 10/1998 | Nobles ....................... | 606/144 |
| 5,891,159 A | | 4/1999 | Sherman et al. ............ | 606/144 |
| 5,947,983 A | * | 9/1999 | Solar et al. ................ | 606/144 |
| 5,964,772 A | | 10/1999 | Bolduc et al. .............. | 606/142 |
| 6,015,416 A | * | 1/2000 | Stefanchik et al. ......... | 606/144 |
| 6,315,784 B1 | * | 11/2001 | Djurovic ..................... | 606/146 |
| 6,514,263 B1 | * | 2/2003 | Stefanchik et al. ......... | 606/144 |

FOREIGN PATENT DOCUMENTS

| | | |
|---|---|---|
| DE | 295962 | 5/1916 |
| DE | 28 01 096 | 7/1978 |
| DE | 34 13744 A1 | 11/1985 |
| DE | 4304353 A1 | 4/1994 |
| DE | 197 04 261 C 2 | 10/1998 |
| FR | 2 713 472 | 6/1995 |

OTHER PUBLICATIONS

Borst C. et al.: "Coronary Artery Bypass Grafting Without Cardiopulmonary Bypass and Without Interruption of Native Coronary Flow Using a Novel Anastomosis Site Restraining Device ('Octopus')", in: J. Am Coll Cardiol 27 (1996), S. 1356–1364.

* cited by examiner

*Primary Examiner*—Anhtuan T. Nguyen
*Assistant Examiner*—Jessica R. Baxter
(74) *Attorney, Agent, or Firm*—Young & Basile, P.C.

(57) ABSTRACT

A device for connecting hollow organs and/or sealing wall defects in hollow organs, has a base mounting for replacement on a hollow organ. The base mounting has at least one recess on a first surface and at least one guidetrack for at least one spiral needle in which the spiral needle is movable forwards in a rotatable fashion. The guidetrack for the spiral needle is disposed at least partially along the edge of the recess in such a manner that the track of the spiral needle during a revolution extends partially in the base mounting and partially in the recess.

29 Claims, 7 Drawing Sheets

DEVICE AND METHOD FOR CONNECTING HOLLOW ORGANS AND/OR SEALING WALL DEFECTS IN HOLLOW ORGANS

The application claims priority of provisional patent application 60/297,127 filed Jun. 8, 2001.

BACKGROUND OF THE INVENTION

The present invention relates to a device and a method for connecting hollow organs and/or sealing wall defects in hollow organs. Such devices and methods are used in the entire field of surgery for connecting hollow organs such as blood vessels or the bowel. These are used particularly in the field of vascular surgery, in particular in the field of bypass surgery in the case of coronary ischaemia for producing proximal or distal anastomoses or also for sealing vascular wall defects. They are used in particular for producing end to end, side to side or end to side anastomoses.

Nowadays, approximately 120,000 bypass operations are performed per year in Germany. The most difficult discipline amongst those are anastomoses on the coronary arteries. It demands a great deal of skill and experience of the surgeon as the vessels here are very small (average arterial diameter 2 mm, vein diameter approximately 4 mm, other transplant diameters for example mammaria 2 mm) and no leakage or suturing to the vascular rear wall must occur.

The manual procedure can be divided into the following operational steps:
1. thoracotomy, sternotomy (opening and cutting through of the sternum);
2. transplant extraction and preparation of the transplant, for example a vein being used as the transplant;
3. putting in of the anastomatic suture with the individual steps of making an incision, preparation of the artery and connection of the transplant opening with the incision opening in the artery; and
4. closure of, the thorax.

In this procedure the connection of the blood vessels by the anastomotic suture represents the most difficult task.

Because there is a danger in this manual connection of suturing to the rear wall of the blood vessel or of leakage. In addition, operations of this type must take place generally on a non-beating heart, which implies additional traumatisation for the patient due to the use of the heart-lung machine.

DE 43 04 353 A1 and also U.S. Pat. No. 5,545,148 A disclose an endoscopic suturing appliance with a helical needle which has one or more windings. This needle is guided in a rotating manner through the edges of a vascular opening which are both held together by clamps and situated opposite each other. In this manner, a spiral suture is put in, the needle pulling a thread through this suture. Finally, the thread ends are then suitably fixed or tied. The spiral needle is thereby freely guided and actuated by two rollers which are located on a handle-like mounting.

SUMMARY OF THE INVENTION

It is the object of the present invention to make available a device and a method for connecting hollow organs and/or for sealing wall defects in hollow organs, by means of which the suturing process can be performed more quickly and more simply and in particular in a high-quality form which is qualitatively reproducible.

This object is achieved by the device and the method disclosed hereinafter. Advantageous developments of the device according to the invention and of the method according to the invention are given as follows:

The device characterized in that the carrier element has suction openings for drawing in a tissue or a hollow organ.

The device is characterized in that the carrier element has an annular configuration.

The device is characterized in that the carrier element extends along the external edge of the first surface.

The device is characterized in that the guidetrack is disposed along the recess in such a manner that the spiral needle can be guided at least partially between two edges of the recess which are situated opposite each other.

The device is characterized in that the guidetrack is disposed in portions along two edges of the recess which are situated opposite each other in such a manner that the portions of the guidetrack which are disposed along the edges of the recess which are situated opposite each other form segments of a single spiral.

The device is characterized in that at least two guidetracks are disposed in the base mounting and, situated opposite each other, extend in and introduced into the artery to be sutured. The probe knife has a probe at its tip which is flexible. In the central part of the probe knife there is located a blade which is aligned by the probe and hence the incision is made in the vascular wall taking into account for example the vascular wall thickness, plaque etc. At the same time, the opening of the base mounting can be orientated by rotation along the probe axis.

The recess in the base mounting has guidetracks which make it possible to position and to hold the transplant-side adapter in a defined manner above this recess. Instead of guidetracks, guidepins or the like or even magnets are possible.

Around the opening in the base mounting there can be located two channels on the underside of the base mounting which respectively form a semicircle and which represent guidetracks for spiral needles. These channels cut the opening such that a wall remains only laterally. On the underside of the wall there are further recesses of the guide tracks which serve as specific guide geometries for the spiral needles. Likewise around the opening, disposed between the recesses, there are located borings near the edge of the recess (opening) through which borings the edges of the incision can be drawn in and held in a defined manner. Further borings for drawing in the base mounting on the tissue are located distributed on the underside of the base mounting or on the annular part of a two-part base mounting.

The base mounting and/or transplant adapter are divisible in the center so that, after completion of the suturing, they can be withdrawn laterally respectively by one of their halves.

The transplant-side adapter also has guidetracks which ensure exact positioning relative to the base mounting. Said adapter has in its center a receiving means (boring) which can draw in the transplant on its external side by means of suction openings which are disposed radially on the internal side of the boring. There are located in addition recesses between the borings through which recesses the spiral needles are guided in a combined state with the base mounting. In this case, the channels of the guidetracks for the spiral needles in the base mounting and this recess in the transplant-side adapter form a common guidetrack for spiral needles.

In the case of the method according to the invention and the device according to the invention, a needle in one variant pulls a thread behind itself, the ends of which are tied to each other in a suitable manner after completion of the suturing.

However, a spiral needle is also conceivable which remains in the suture as a thread replacement. The needle can then also be made of biodegradable materials.

With the device according to the invention and the method according to the invention, in particular leakages of the suture and also suturing to the rear wall of the coronary artery can be avoided. Occlusions of the artery can thus be avoided. In addition, the base mounting stabilizes the coronary artery by suction of the coronary artery and of the tissue surrounding it so that if necessary an operation can be performed also on a beating heart. The device according to the invention is suitable in addition for minimally invasive use, it being able to be introduced in this case into the body via small accesses without opening up the thorax. In addition, the artery and transplantside part of the instrument, i.e. the base mounting and the adapter can be introduced into the body by means of a trocar and be operated endoscopically. The device according to the invention is also suitable for manipulation by a robot as long as the adaptation of the tool is configured appropriately.

The conception of the device according to the invention achieves the object of applying anastomoses (connection of hollow organs). Its field of application is first of all bypass surgery on the heart in the case of coronary ischaemia, however also in addition on other organs in the case of stenoses, occlusions, contractions and thromboses in peripheral arteries and generally for sealing openings in hollow organs. With the device according to the invention both proximal and distal anastomoses can be applied in coronary artery bypass surgery (CABG, coronary artery bypass operation). Furthermore, applying an anastomosis can be effected with the mammaria as the transplant.

BRIEF DESCRIPTION OF THE DRAWINGS

A few examples of devices and methods according to the invention are described subsequently.

DESCRIPTION OF THE PREFERRED EMBODIMENT

Figure 1:
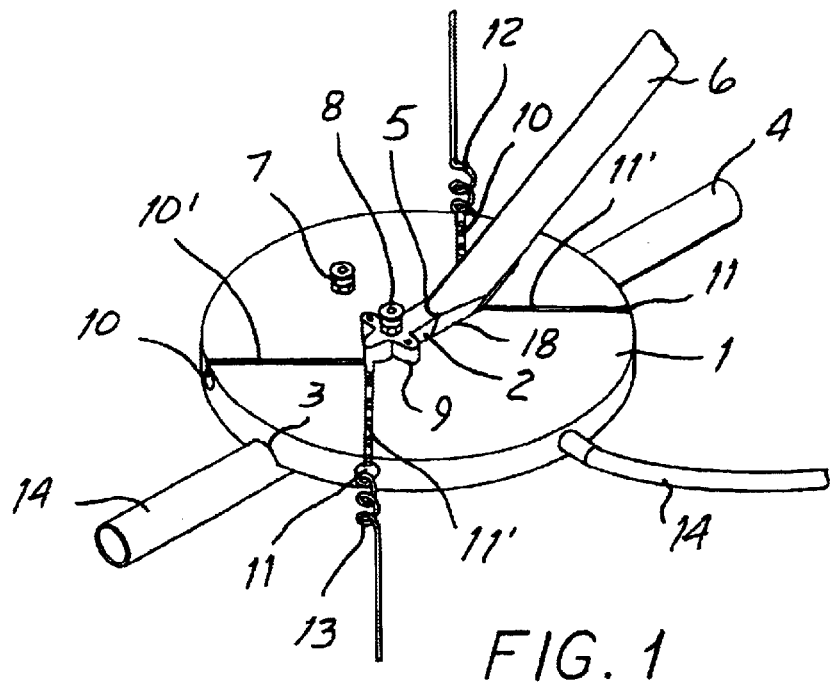
FIG. 1 shows a base mounting according to the invention with adapter.

FIG. 1 shows a base mounting 1 according to the invention with adapter 2. The base mounting 1 is placed on an artery 4 and fixed by suction holes. By means of appropriate openings in the underside of the base mounting 1, which are not illustrated here, the base mounting 1 can now be drawn in and fixed to the heart muscle above the artery 4. The base mounting need not necessarily however have a channel-like recess 3. The artery can also be drawn in only after the heart muscle and via a separate suction device.

Figure 5:
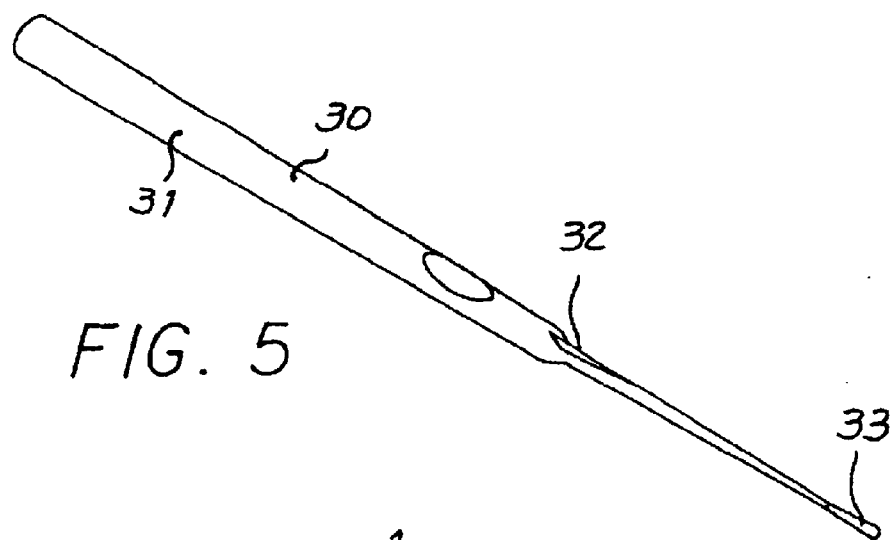
FIG. 5 shows a probe knife.

By means of a small cut in the artery, the configuration of the artery can now be determined by means of a probe, as is illustrated for example in FIG. 5. The probe is provided with a cutting mechanism in order to make an incision in the artery along the probe direction, the incision being delimited by the opening 18 (see FIGS. 2A–B) in the base mounting 1.

In addition, the base mounting has two guidetracks 10, 11 which are introduced as a boring in the base mounting 1. These guidetracks serve for guiding the spiral needles 12, 13. The actuation of the spiral needles is effected within the base mounting via the access 14, for example a flexible shaft.

An adapter 2 is introduced into the opening 18 of the base mounting 1 and has for its part an opening 5. A piece of a vein 6 is introduced as a transplant into the opening 5.

Both the base mounting 1 and the adapter 2 have one connection piece 7, 8, respectively, to which low pressure tubes can be connected. In this way, a low pressure can be applied to corresponding openings along the circumference of the recess 18 or of the opening 5 in order to draw in and to fix the edge of the incision in the artery or the edge along the open end of the vein 6.

Figure 2A:
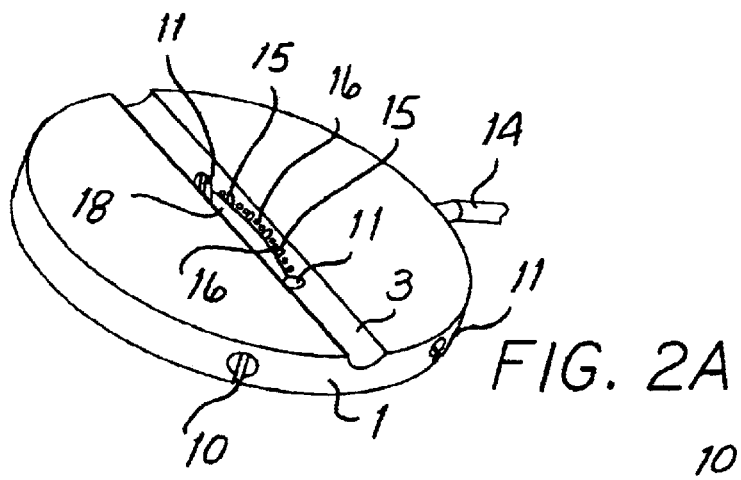
FIGS. 2a–b show the base mounting according to the invention.
Figure 2B:
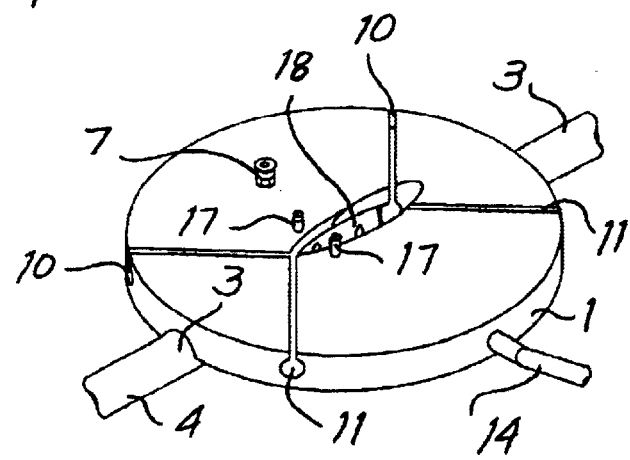

FIG. 2 shows the base mounting 1 of FIG. 1 on the one hand viewed from below (FIG. 2A) and also in plan view (FIG. 2B). Here, as in the following, identical or corresponding elements are provided with identical or corresponding reference numbers.

It can be detected in FIG. 2A that the edge of the recess 18 has openings 15 on the one hand which represent guidetracks for a spiral needle. This means that the guidetracks 15 themselves are portions (segments) of a single spiral configuration so that a spiral runs through all of these segments 15 of the guidetrack during a rotating forward movement. Furthermore, both borings of the guidetrack 11 are illustrated which extend out with the recess 18 within the base mounting 1 and receive the spiral.

In FIG. 2B, two guidepins 17 can be detected furthermore on the surface of the base mounting to the left and the right of the recess 18, which guidepins engage in corresponding borings in a guide element 9 of the adapter 2 and thus ensure a safe and correct fit of the adapter 2 in the base mounting 1.

Figure 3A:
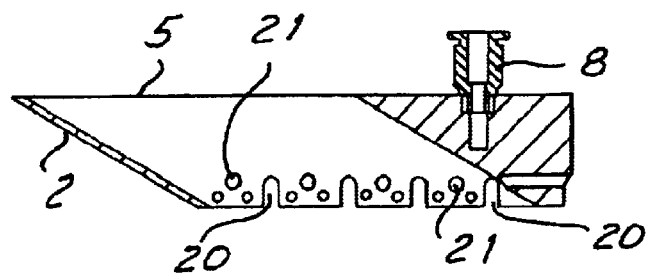
FIGS. 3a–b show the adapter according to the invention.
Figure 3B:
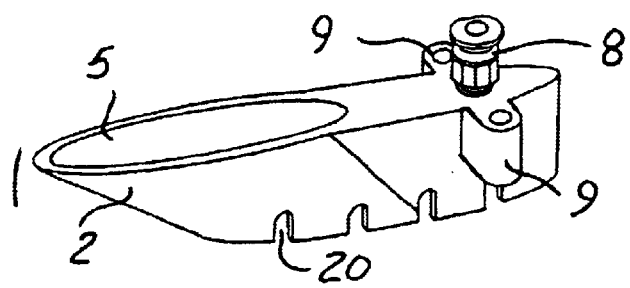

FIGS. 3A–B show the adapter 2 in both partial pictures A and B, in side view (FIG. 3A) and in diagonal view (FIG. 3B). The adapter 2 has a diagonally extending boring 5 into which a transplant can be introduced. On its lower end, which terminates approximately with the underside of the base mounting 1 in the inserted state, there are likewise provided guidetracks 20 for a spiral needle. These guidetracks are disposed in such a manner that they form with the guidetracks 15 in the base mounting a common guide for a spiral needle. Furthermore, there are located in this region suction openings 21 via which the edge of a transplant located in the opening 5 is drawn in and fixed to the external wall of the boring 5 in the adapter 2.

Figure 4A:
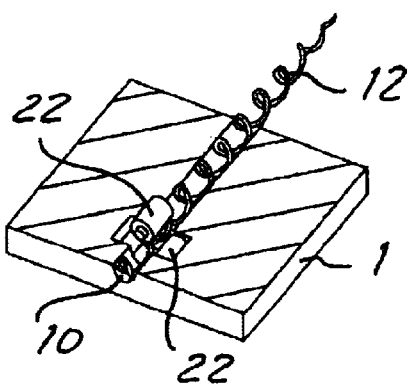
FIGS. 4a–c shows three variants for a drive of a spiral needle.
Figure 4B:
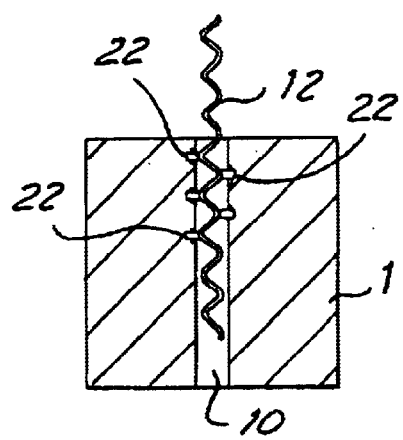
Figure 4C:
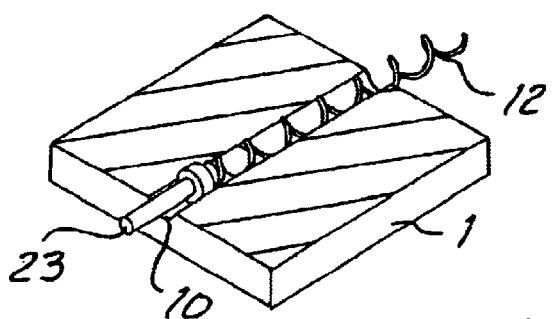

FIGS. 4A–C show various possibilities for the drive of a spiral needle within the base mounting 1. The spiral needle 12 is located already within the spiral needle guide 10 in FIGS. 4A to C.

In FIG. 4A, there are located beside the boring 10 in total three rollers 22 which are disposed in such a manner that their axis of rotation is located parallel to the boring 10. The rollers 22 are in addition disposed beside the boring 10 in such a manner that they remain in frictional contact in one of the spiral needles guided by the boring 10. If the rollers 22 are now actuated, then the spiral 12 is rotated and moves thereby forwards in addition.

A view is shown in FIG. 4B in which in total five rollers 22 are used.

In FIG. 4C, an actuation principle is chosen in which a shaft 23 is in non-positive contact with the rear end of the spiral needle. The shaft 23 is now rotated and at the same time pushed forwards so that the spiral needle is moved forwards while rotating.

FIG. 5 shows a probe knife 30 with a handle 31 and a probe 33. Above the probe 33 in the direction of the handle 31 there is situated a knife edge 32 in the probe knife.

The probe can be introduced into a vessel and be aligned therein. If the probe 30 is aligned then an incision into the vessel can take place from inside by cutting through the vascular wall with the knife 32. In the case of an incision of this type, which is made within the recess 18 of the base mounting 1 into a vessel 3, the length of the incision is delimited by the size of the recess 18 in the base mounting 1.

Figure 6A:
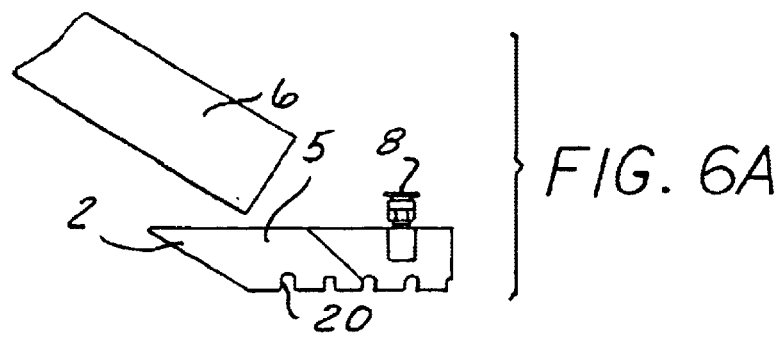
FIGS. 6a–c show the preparation of a transplant.
Figure 6B:
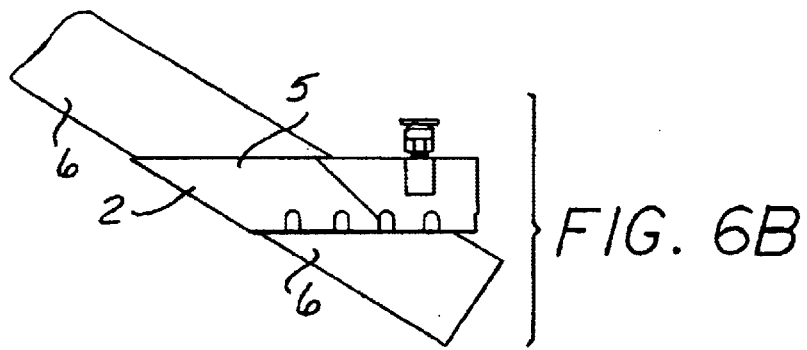
Figure 6C:
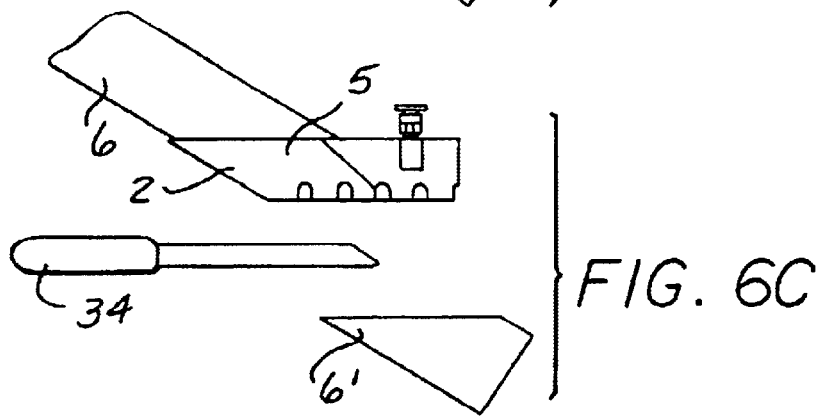

FIGS. 6A–C show the preparation of a transplant 6. For this purpose a transplant 6, for example a vein, is introduced into the opening 5 of the adapter 2. This is illustrated in FIGS. 6A and 6B. Next the transplant can be fixed to the wall of the boring 5 by suction, as is illustrated for example in FIGS. 3A–B. The projecting portion of the transplant which projects downwardly over the adapter 2, is then cut off by a knife 34 along the lower edge of the adapter 2. This projecting portion 6 is then disposed of.

The proximal end of the transplant can however be effected via a type of template or limit stop corresponding to the incision on the artery.

Figure 7:
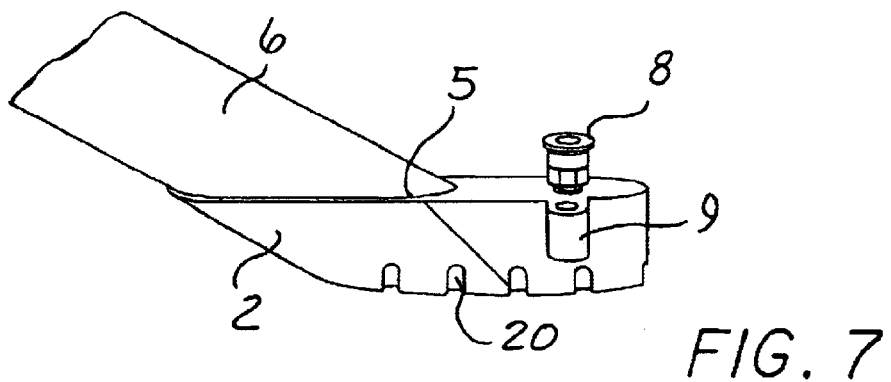
FIG. 7 shows an adapter with transplant.

FIG. 7 shows the transplant 6 which is prepared and fixed in the adapter 2.

Figure 8:
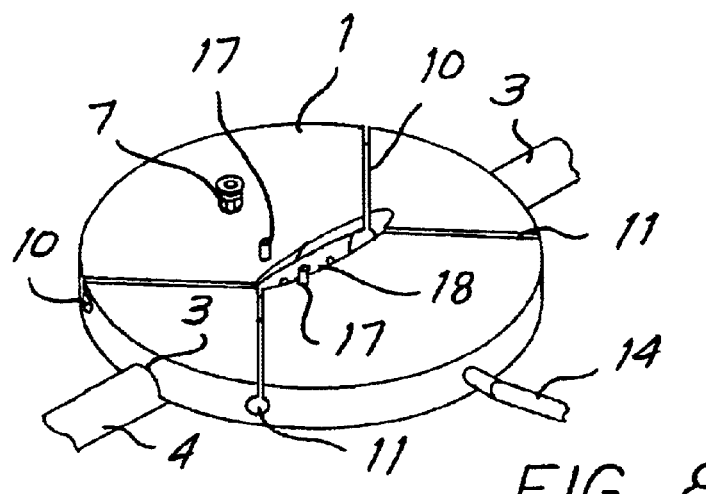
FIG. 8 shows a base mounting with artery.

Next the base mounting 1 is positioned as illustrated in FIG. 8 at a suitable position above a desired artery on the heart muscle and there is drawn in to the heart muscle via openings in the lower side of the base mounting 1 (not illustrated here).

Now the course of the artery is determined by a small cut by means of the knife probe 30. Advantageously, the base mounting 1 can be mounted rotatably and then be aligned correspondingly to the probe axis. This position is then fixed and the incision is made in the artery 4 along the probe direction within the recess 18 of the base mounting 1. The opening 18 in the base mounting 1 thereby delimits the size or length of the incision. Next the artery is drawn in and fixed in this position.

Figure 9:
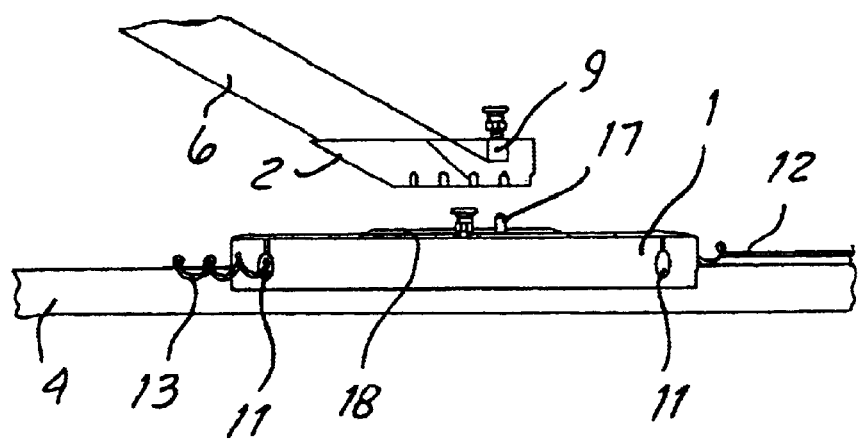
FIG. 9 shows a side view of a base mounting and of an adapter.

FIG. 9 now shows how the transplant-side adapter 2 is placed on the base mounting 1. In order to achieve the exact position, pins 17 of the base mounting 1 are thereby used which correspond to the borings in the guide 9 of the adapter 2.

Next the spiral needles 12 and 13 are introduced into their corresponding needle guidetracks 10 or 11.

Figure 10:
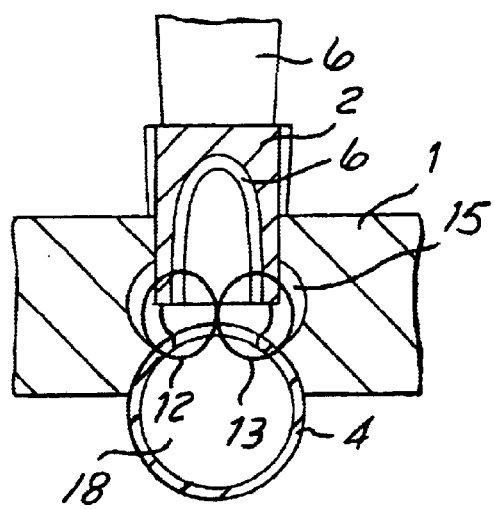
FIG. 10 shows a further section through a base mounting and an adapter.

FIG. 10 shows a cross-section through a base mounting 1 with adapter 2 while inserted in each other, the spiral needles 12 and 13 also being illustrated here. As can be detected, the spiral needles 12 and 13 are guided through guides 15 partly in the base mounting 1, partly in the adapter 2 and partly in the free space of the recess 18. They thereby catch also the wall of the artery 14 and the wall of the vein 6.

The needles 12 and 13 are guided through the wall of the base mounting 1 in a semicircular fashion around the recess 18. A spiral suture is thereby produced.

On the one hand, the spirals can remain after introducing the spirals into the edges of the vascular openings and thus can form the suture. On the other hand, the needles can be pushed out again from the transplant and the artery, said needles pulling a thread secured on their rear end through the holes in the artery and the vein wall. The resulting thread pairs can then be tied to each other.

Figure 11A:
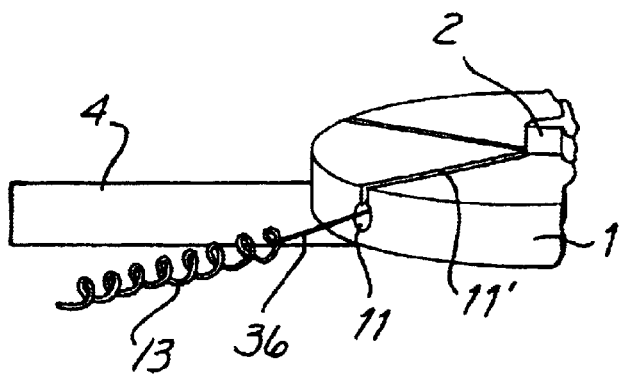
FIGS. 11a–b shows suturing of an anastomosis.
Figure 11B:
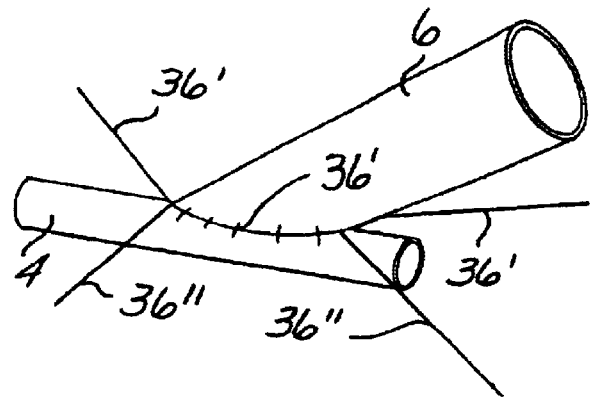

FIGS. 11A–B show how the needle 13 is extracted from its needle guide 11, said needle pulling a thread behind itself. The boring 11 and also the boring 10 in the above Figures are connected to the upper side of the base mounting via slots in an open manner. Through these slots 10', 11' the thread can now be taken out upwardly and tied together as is shown in FIG. 11B so that a clean suture which connects the edges of the incision in the artery 4 to the vascular edges of the vein 6 is produced.

It is advantageous in the method according to the invention that the endothelium of the vessels 4 and 6 is not damaged during the method according to the invention and thus an optimal wound healing can be made possible.

As can be readily detected in FIG. 11B, the threads 36', 36" are guided in a semicircle around the incision in the artery 4, said threads overlapping at two places and being able to be tied there.

Figure 12:
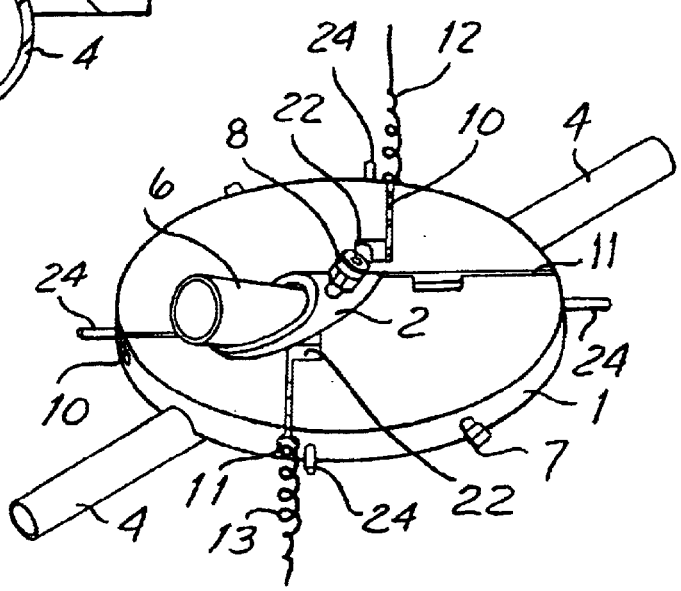
FIG. 12 shows a base mounting and an adapter.

FIG. 12 shows a further base mounting with adapter 2. Next to the borings 10 and 11 for guiding the spiral needles, rollers 22 are disposed respectively now underneath openings in the base mounting, said rollers being actuated via shafts 24. These rollers correspond to those from FIG. 4A and serve for actuation of the spiral needles 12 and 13.

Figure 13A:
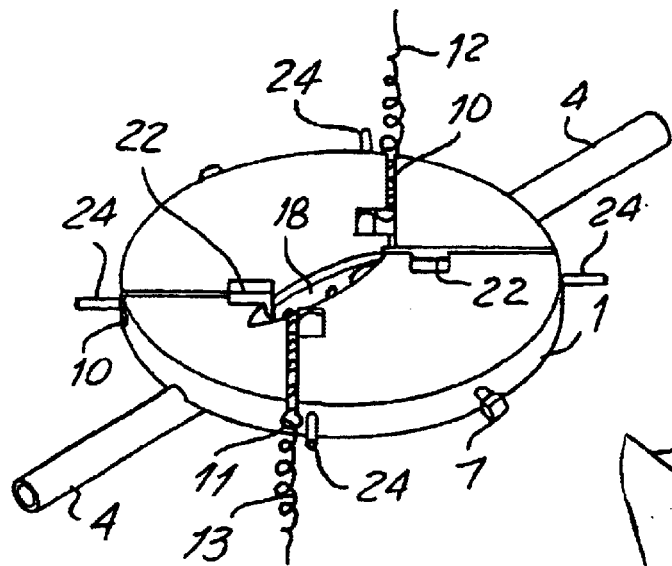
FIGS. 13a–b show a further base mounting.
Figure 13B:
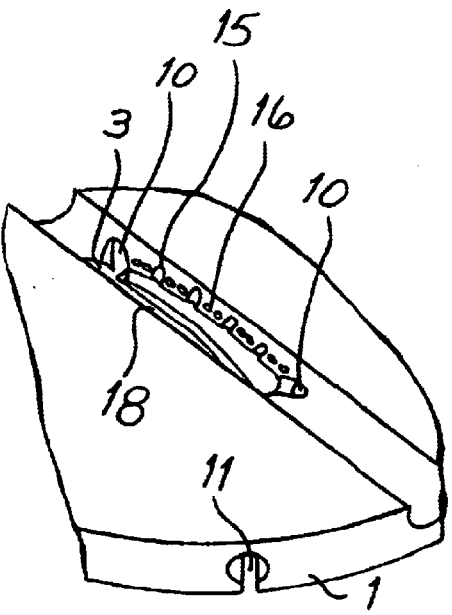

FIG. 13A shows the base mounting of the previous Figure without insertion of the adapter 2, while FIG. 13B represents the underside of this base mounting 1. It can be detected how the borings 10 and suitable guides are provided along the edge of the recess 18 for guiding the helical spiral needle. The spiral needles penetrate furthermore into borings 15 which likewise serve for their guidance. Furthermore, openings 16 are illustrated on the edge of the channel-shaped recess 3 towards the underside of the base mounting 1, via which openings low pressure can be applied to the edge of the incision in the artery.

Figure 14:
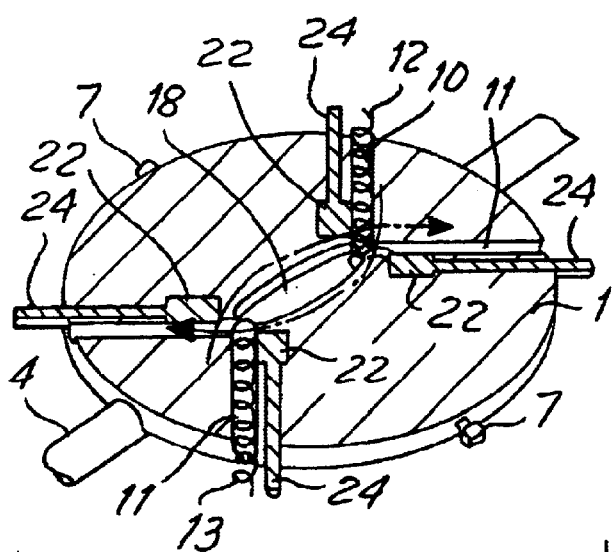
FIG. 14 shows a section through a base mounting.

FIG. 14 illustrates once again this base mounting from above, the paths of the spiral needles 12 or 13 being illustrated with the two arrows. It can be detected that in this sectioned illustration of the base mounting 1 the spiral needles 12 and 13 perform circular movements here which intersect each other. As the spiral needle cross each other, the two spiral needles and hence the two sutures are guided and introduced successively around the opening 18.

Figure 15:
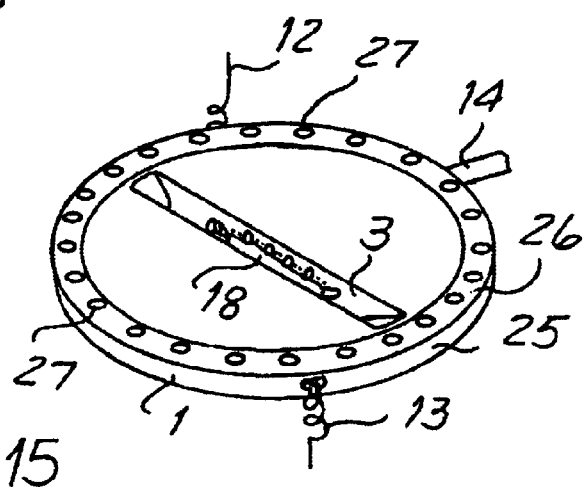
FIG. 15 shows a view from below of the base mounting.

FIG. 15 shows a further example of a base mounting 1, this being illustrated in bottom view. On the base mounting 1 there is now situated a ring 26 with openings 27 via which low pressure can be applied to a tissue or to a heart muscle. As a result, the base mounting 1 is fixed to the heart muscle. As the ring 26 and the upper part 25 of the base mounting 1 are rotatable relative to each other, the vein 3 can then be aligned along an artery and fixed.

This alignment and attachment can be effected by introducing the probe into the artery and indicating its orientation.

Figure 16:
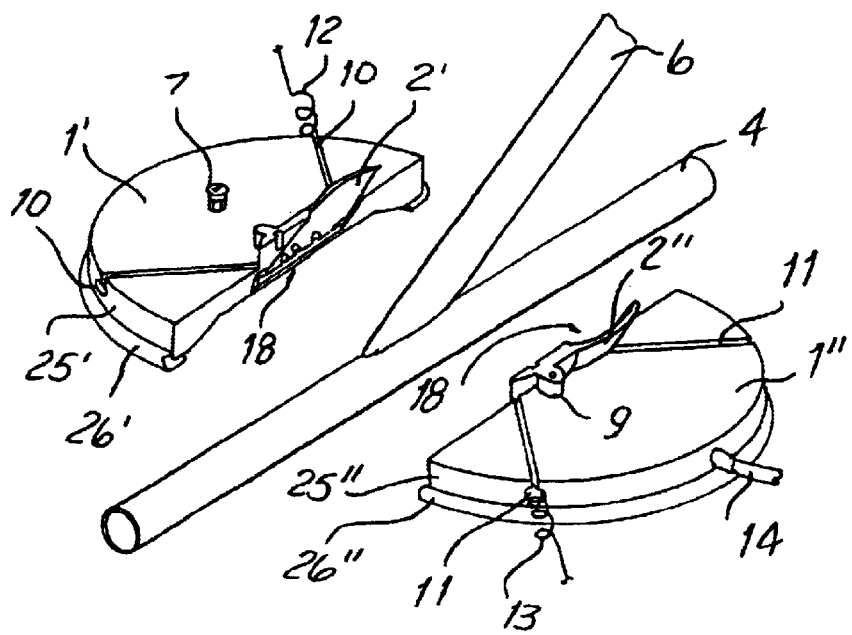
FIG. 16 shows a divided base mounting.

FIG. 16 shows a base mounting 1 and an adapter 2 which are divided in two, i.e. can be separated along the recess 18 into two halves 1', 1"or 2', 2". As a result, the base mounting and also the adapter can be removed after suturing of the vein 6 to the artery 4 has been completed.

In the present example of FIG. 16, a ring 26' is also disposed underneath the base mounting 1, via which ring the upper part 25' of the base mounting 1 can be rotated relative to the ring 26'. As a result, after the ring 26' has been drawn in to the heart muscle, the recess 18 can also be adapted exactly to the artery 4 and its direction.

Figure 17:
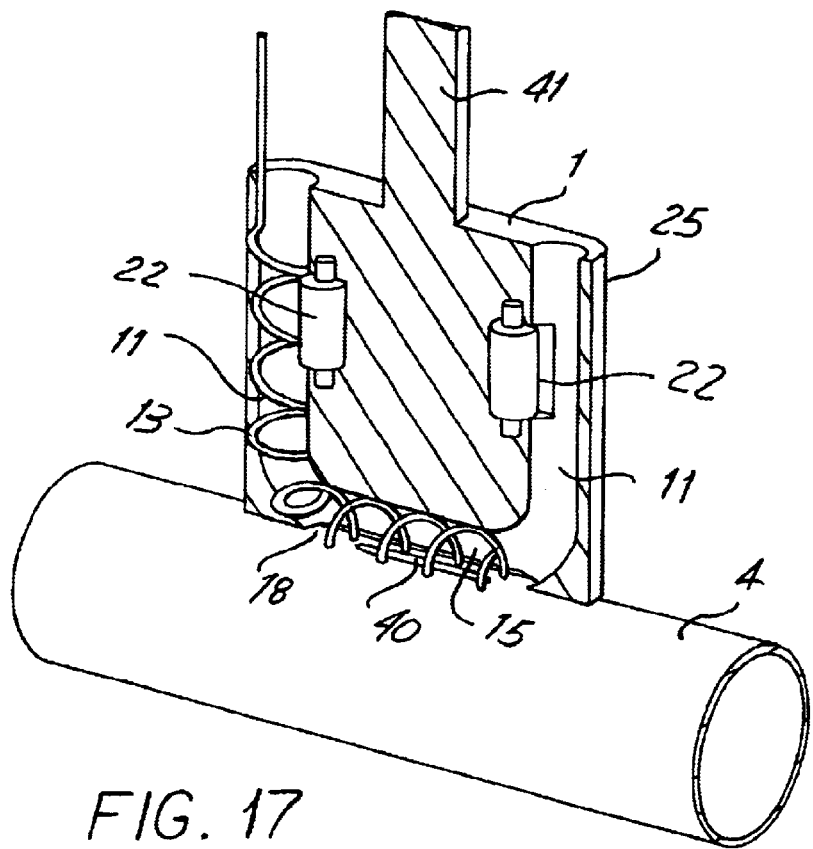
FIG. 17 shows a device for sealing a vascular wall defect.

FIG. 17 shows a further embodiment for sealing an opening in a hollow organ wall. The opening 40, for example an incision into an artery, is thereby likewise pierced by means of a spiral needle, the spiral needle going through both edges of the incision 40. After the spiral has passed through the edges of the incision 40, a thread is pulled through the thus pierced openings in the vascular wall by the spiral and then is tied.

In this case, a base mounting 1 occurs once again which has a guide 11 for a spiral needle 13. The spiral needle is thereby guided once again by the guide 11 in the region of an opening 18 partially within the base mounting and partially out with the base mounting in the recess 18. The channel 11, 15 thereby cuts the opening 18 such that there remains only a wall running laterally. On the underside of the wall, hollows can also be disposed which serve as guide geometries for the spiral needle. Here too, around the opening 18, for example between the recesses, borings can be provided close to the edge of the recess 18 through which the edges of the wall opening of the hollow organ can be drawn in and be held in a defined manner.

What is claimed is:

1. A device for at least one of connecting hollow organs and sealing wall defects in hollow organs, having a base mounting which has at least one recess on a first surface;
   at least one guidetrack for at least one spiral needle in which a spiral needle is movable forwards in a rotatable fashion;
   the guidetrack for the spiral needle being disposed at least partially along the edge of the recess in such a manner that the track of the spiral needle during a revolution extends partially in the base mounting and partially in the recess;
   wherein at least two guidetracks are disposed in the base mounting and, situated opposite each other, extend in a region of the recess along two edges of the recess which are situated opposite each other; and
   wherein the two guidetracks intersect each other at least at one of the beginning and at the end of their course along the recess.

2. The device according to claim 1, wherein the guidetrack in a region at a distance from at least one of the recess and in the region along the edge of the recess has the configuration of a spiral or of circular segments of a spiral.

3. The device according to claim 2, wherein the guidetrack in the region along the edge of the recess has the configuration of circular segments of a spiral, the respective ends of which form openings in the base mounting along the edge of the recess.

4. The device according to claim 2, wherein the guidetrack in the region at a distance from at least one of the recess and in the region along the recess has the configuration of a spiral or of circular segments of a spiral and has an internal diameter which is greater than or equal to the diameter of a spiral needle.

5. The device according to claim 1, wherein the guidetrack in the region at a distance from the recess is configured as a boring with an internal diameter which is greater than or equal to the external diameter of the spiral formed by the spiral needle.

6. The device according to claim 1, wherein at least in portions along the recess on the surface of the base mounting there are disposed suction openings for drawing in and fixing the edges of an opening of a hollow organ.

7. The device according to claim 1, wherein along the guidetrack there is disposed at least one roller, the axis of rotation of which is essentially parallel to the direction of passage of the guidetrack.

8. The device according to claim 7, wherein the roller is connected to a drive in a non-positive manner for rotation of the roller.

9. The device according to claim 1, wherein the guidetrack in the region outside the recess along its direction of passage is opened towards a second surface of the base mounting which is situated opposite the first surface.

10. The device according to claim 9, wherein between the second surface and the guidetrack, a slot is disposed along the guidetrack.

11. The device according to claim 9, wherein the recess extends from the first to the second surface.

12. The device according to claim 1, wherein at least along the recess, the surface of the base mounting has a recess for receiving a hollow organ.

13. The device according to claim 1, wherein on the first surface, suction openings are disposed for drawing in at least one of tissue and a hollow organ.

14. The device according to claim 1, wherein the base mounting has a ring on its side orientated towards the first surface, which the ring is mounted rotatably on the base mounting.

15. The device according to claim 14, wherein the carrier element has suction openings for drawing in a tissue or a hollow organ.

16. The device according to claim 14, wherein the carrier element has an annular configuration.

17. The device according to claim 16, wherein the ring extends along the external edge of the first surface.

18. The device according to claim 1, wherein the guidetrack is disposed along the recess in such a manner that the spiral needle can be guided at least partially between two edges of the recess which are situated opposite each other.

19. The device according to claim 18, wherein the guidetrack is disposed in portions along two edges of the recess which are situated opposite each other in such a manner that the portions of the guidetrack which are disposed along the edges of the recess which are situated opposite each other form segments of a single spiral.

20. The device according to claim 1, wherein an adapter element is configured so as to be engagable at least partially in a form fitting manner from the direction of the second surface into the recess.

21. The device according to claim 20, wherein the adapter element has a boring for receiving a hollow organ portion, which boring extends from the side orientated towards the base mounting to the side orientated away from the base mounting.

22. The device according to claim 21, wherein the longitudinal axis of the boring extends at a predetermined angle relative to the first surface.

23. The device according to claim 22, wherein the walls of the boring have at least one guidetrack which completes that at least one guidetrack of the base mounting to form a common guidetrack for a spiral needle.

24. The device according to claim 21, wherein the walls of the boring have suction openings for drawing in and fixing a hollow organ portion or its edge.

25. The device according to claim 20, wherein at least one of the base mounting and the adapter element can be divided into at least two parts along the recess.

26. The method for at least one of connecting hollow organs and for sealing wall defects in hollow organs, characterized in that by using a device according to claim 1, comprising the step of guiding at least one spiral needle in a rotating manner through the adjacent edges of the same or of two different hollow organ openings.

27. The method according to claim 26 further comprising the step on pulling a thread through the edge of the opening of the hollow organ with each spiral needle.

28. The method according to claim 27 further comprising the steps of removing the spiral needle and connecting thread ends to each other.

29. The method according to claim 28 comprising the step of tying the thread ends to each other.

* * * * *